United States Patent
Cotton et al.

(10) Patent No.: US 6,303,788 B1
(45) Date of Patent: Oct. 16, 2001

(54) PROCESS FOR PREPARING OMEPRZOLE

(75) Inventors: Hanna Cotton, Årsta; Magnus Larsson, Bromma; Anders Mattson, Täby, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/194,647

(22) PCT Filed: Nov. 3, 1998

(86) PCT No.: PCT/SE98/01984

§ 371 Date: Dec. 1, 1998

§ 102(e) Date: Dec. 1, 1998

(87) PCT Pub. No.: WO99/25711

PCT Pub. Date: May 27, 1999

(30) Foreign Application Priority Data

Nov. 14, 1997 (SE) .................................................. 9704183

(51) Int. Cl.$^7$ .................................................. C07D 401/12
(52) U.S. Cl. .......................................................... 546/273.7
(58) Field of Search ........................................... 546/273.7

(56) References Cited

U.S. PATENT DOCUMENTS 5,386,032  1/1995  Brändström ........................ 546/273.7
5,391,752  2/1995  Hoerrner et al. .................. 546/273.7
5,948,789 * 9/1999  Larsson et al. .................... 546/273.7

FOREIGN PATENT DOCUMENTS 0005129  10/1979  (EP) .
9602535  2/1996  (WO) .

OTHER PUBLICATIONS

CA 96:180441, Bortolini et al., 1982.*
CA 105:172748, Bortolini et al., 1986.*
CA 119: 159794, Komatsu et al., 1993.*
CA 120: 269745, Choudary et al., 1994.*
CA 125:166890, Di Furia et al., 1996.*

* cited by examiner

Primary Examiner—Jane Fan
(74) Attorney, Agent, or Firm—White & Case LLP

(57) ABSTRACT

The present invention relates to a novel process for the synthesis of 5-methoxy-2-[[(4-methoxy-3,5-dimethyl-2-pyridinyl)methyl]sulfinyl]-1H-benzimidazole, known under the generic name omeprazole. Moreover, the present invention also relates to manufacture of a pharmaceutical preparation thereof and its use in medicine.

The novel process for the preparation of omeprazole, comprises the step of oxidizing 5-methoxy-2-[[(4-methoxy-3,5-dimethyl-2-pyridinyl)methyl]thio]-1H-benzimidazole in an organic solvent with an oxidizing agent in the presence of a titanium complex and optionally in the presence of a base.

15 Claims, No Drawings

PROCESS FOR PREPARING OMEPRZOLE

FIELD OF THE INVENTION

The present invention relates to a novel process for the preparation of 5-methoxy-2-[[(4-methoxy-3,5-dimethyl-2-pyridinyl)methyl]sulfinyl]-1H-benzimidazole, known under the generic name omeprazole. Moreover, the present invention also relates to the manufacture of a pharmaceutical preparation thereof and its use in medicine.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole, having the generic name omeprazole, is a proton pump inhibitor, i.e. effective in inhibiting gastric acid secretion, and is useful as an antiulcer agent. In a more general sense, omeprazole may be used for treatment of gastric-acid related diseases in mammals and especially in man.

Omeprazole and therapeutically acceptable salts thereof, are described in EP 5 129. This patent also discloses a process for the preparation of omeprazole and other structurally related substituted benzimidazoles.

U.S. Pat. No. 5,386,032 describes an improved process for synthesis of omeprazole. This process describes the oxidation step and a work-up procedure for omeprazole. The oxidation step utilizes m-chloroperoxybenzoic acid in a solvent system consisting of an organic solvent and an aqueous phase of constant pH. The work-up procedure includes an extraction step and precipitation of omeprazole by the addition of an alkyl formate to the aqueous phase.

Another alternative process for the manufacture of omeprazole is described in U.S. Pat. No. 5,391,752. This process utilizes magnesium monoperoxyphtalate as an oxidizing agent.

Omeprazole is a sulfoxide and a chiral compound, with the sulfur atom being the stereogenic center. Thus, omeprazole is a racemic mixture of its two single enantiomers, the R and S-enantiomer of omeprazole. An enantioselective process for the synthesis of the single enantiomers of omeprazole is described in WO 96/02535. The asymmetric oxidation utilizes a chiral titanium complex to induce the chirality.

In the light of the above there was still a need for a new convenient and more efficient process for the manufacture of racemic omeprazole.

SUMMARY OF THE INVENTION

The object of the present invention is to provide a novel process for the preparation of omeprazole. In the present invention, 5-methoxy-2-[[(4-methoxy-3,5-dimethyl-2-pyridinyl)methyl]thio]-1H-benzimidazole is oxidized to omeprazole in an organic solvent with an oxidizing agent in the presence of a titanium complex, and optionally in the presence of a base. The present invention is further characterized in that omeprazole precipitates from the reaction mixture. Omeprazole, substantially free from titanium salts, can thereafter easily be filtered of from the reaction mixture and thereby avoiding time consuming steps, such as work up procedures including extraction. This precipitation of omeprazole from the reaction mixture is unexpected since the corresponding single enantiomers of omeprazole does not precipitate from the reaction mixture if the same reaction conditions are used.

This precipitation of omeprazole from the reaction mixture is advantageous and the present invention is the first process described for the preparation of omeprazole involving no extraction step. The precipitation of omeprazole results in a number of further advantages. Omeprazole is sensitive towards acid and over-oxidation, i.e. oxidation from sulfoxide to sulfone. However, since both these reactions take place in the solution phase, they are both suppressed by the fact that omeprazole precipitates from the reaction mixture. This precipitation of omeprazole also suppresses other potential side-reactions, such as thermal decomposition of omeprazole.

The titanium complex suitable for catalysing the process of the present invention is prepared from a ligand and a titanium(IV) compound, preferably a titanium(IV)alkoxide, and optionally in the presence of additional water. An especially preferred titanium(IV)alkoxide is titanium(IV) isopropoxide or -propoxide. The amount of the titanium complex used in the present invention is not critical. An amount of less than approximately 0.50 equivalents, in proportion to the sulfide, is preferred and an especially preferred amount is 0.05–0.30 equivalents. However, less than 0.05 equivalents could also be used and the lower limit of 0.05 equivalents is only given for handling reasons.

The ligand used in the present invention to produce the titanium complex can be either an achiral or a chiral ligand of which the latter is preferred. Useful ligands are alcohols, such as diols, and preferably vicinal diols. The diol may be a branched or unbranched alkyl diol, or an aromatic diol. Preferred diols are esters of tartaric acid, such as ethyl esters.

The titanium complex may also be prepared by reacting titanium tetrachloride with a suitable ligand in the presence of a base.

The present invention is further characterized by that an achiral ligand or a mixture of stereoisomers, such as a mixture of enantiomers, of a chiral ligand is used. All mixtures including a racemic mixture is within the scope of the present invention.

In a preferred aspect of the present invention a racemic mixture of chiral ligands is used to prepare the titanium complex.

The oxidizing agent used is not crucial and can be selected to suit the reaction conditions and equipment used. Examples of such oxidizing agents include, but are not limited to, peroxyacides, such as m-chloroperoxybenzoic acid, and peroxides, such as cumene hydroperoxide, tert-butyl hydroperoxide and hydrogen peroxide. One advantage of the present invention is that a less reactive and less corrosive oxidizing agent can be used to prepare omeprazole compared to those used in the prior art. The amount of oxidizing agent used according to the present invention is preferably approximately one equivalent, such as 0.9 to 1.05 equivalents, in proportion to the sulfide.

According to a preferred aspect of the invention, cumene hydroperoxide or tert-butyl hydroperoxide are used as oxidizing agent.

According to one aspect of the invention the oxidation is carried out in the presence of a base, such as 0.05–1.0 equivalents, preferably 0.15 0.3 equivalents. Optionally, the oxidation can be carried out in the absence of a base.

The base may be an inorganic or an organic base. Organic bases are preferred and especially suitable bases are amines, preferably triethylamine or N,N-diisopropylethylamine. The amount of base added to the reaction mixture is not crucial.

The oxidation is preferably carried out in an organic solvent around room temperature or above, e.g. between 10–60° C. Suitable organic solvents are for instance toluene, ethyl acetate, and the like. Toluene is the preferred solvent.

The order in which the reactants, i.e. the titanium compound, the ligand, the base, the solvent, water, and the 5-methoxy-2-[[(4-methoxy-3,5-dimethyl-2-pyridinyl) methyl]thio]-1H-benzimidazole, are charged into the reaction vessel is not crucial and should be adapted to suit the equipment used. It is however preferred that all reactants are loaded into the reaction vessel before the oxidizing agent is added.

The preparation of the titanium complex may be performed at room temperature or at an elevated temperature and/or during a prolonged preparation time and in the presence or absence of 5-methoxy-2-[[(4-methoxy-3,5-dimethyl-2-pyridinyl)methyl]thio]-1H-benzimidazole.

According to one aspect of the present invention the titanium complex is prepared in the presence of 5-methoxy-2-[[(4-methoxy-3,5-dimethyl-2-pyridinyl)methyl]thio]-1H-benzimidazole.

An advantage of the process according to the present invention is that omeprazole precipitates from the reaction mixture without simultaneous precipitation of titanium salts. Due to this precipitation, omeprazole can be easily separated from the reaction mixture by filtration or centrifugation and thereby avoiding any time consuming work-up procedure.

The process of the present invention may also be used to produce not only omeprazole but also other substituted sulfinyl heterocyclic compounds known in the art, such as compounds with the generic names lansoprazole, pantoprazole, leminoprazole and rabeprazole.

The following example which will further illustrate the invention, but is not intended to limit the scope of the invention as defined hereinabove or as claimed below.

EXAMPLE

5-Methoxy-2-[[(4-methoxy-3,5-dimethyl-2-pyridinyl) methyl]thio]-1H-benzimidazole (15.4 g, 46.7 mmol) was dissolved in toluene (70 ml). The solution was heated to 50° C. and water (0.030 ml) was added. To the resulting mixture was added diethyl(D,L)-tartrate (2.02 g, 9.78 mmol) in toluene (8 ml) and titanium(IV)isopropoxide (1.33 g, 4.68 mmol). The mixture was cooled to 30° C. and diisopropylethylamine (0.962 g, 7.44 mmol) was added followed by cumene hydroperoxide (8.21 g, 53.9 mmol). The mixture was stirred at 30° C. for 5 h and the precipitated product was filtered off and washed with toluene (12 ml). Yield: 13.1 g (81%).

What is claimed is:

1. An improved process for the preparation of racemic omeprazole, comprising the step of oxidizing 5-methoxy-2-[[(4-methoxy-3,5-dimethyl-2-pyridinyl)methyl]thio]-1H-benzimidazole in an organic solvent with an oxidizing agent and optionally in the presence of a base, wherein the improvement is that the oxidation is performed in the presence of a titanium complex produced from an achiral ligand or a racemic mixture of chiral ligands and wherein the racemic omeprazole product is recovered by precipitation.

2. The process according to claim 1, wherein the oxidation is performed in the presence of a base.

3. The process according to claim 1 or 2, wherein the titanium complex is prepared from a titanium(IV) compound and the ligand(s).

4. The process according to claim 1, wherein the titanium complex is produced from an achiral ligand.

5. The process according to claim 1, wherein the titanium complex is prepared in the presence of 5-methoxy-2-[[(4-methoxy-3,5-dimethyl-2-pyridinyl)-methyl]thio]-1H-benzimidazole.

6. The process according to claim 1, wherein the organic solvent is toluene.

7. The process according to claim 1, or 2 wherein the base is triethylamine or N,N-diisopropylethylamine.

8. The process according to claim 3, wherein the titanium compound is a titanium(IV)alkoxide.

9. The process according to claim 8, wherein the titanium compound is titanium(IV)isopropoxide.

10. The process according to claim 1, wherein the titanium complex is produced from a racemic mixture of chiral ligands.

11. The process according to claim 3, wherein the ligand is an alcohol.

12. The process according to claim 11, wherein the ligand is an ester of tartaric acid.

13. The process according to claim 1, wherein the oxidizing agent is a peroxide.

14. The process according to claim 1, wherein the oxidizing agent is a peroxyacid.

15. The process according to claim 13, wherein the oxidizing agent is cumene hydroperoxide or tert-butyl hydroperoxide.

* * * * *